(12) United States Patent
Liu et al.

(10) Patent No.: US 10,851,100 B2
(45) Date of Patent: Dec. 1, 2020

(54) PREPARATION METHOD FOR AND INTERMEDIATE OF PYRROLO SIX-MEMBERED HETEROAROMATIC RING DERIVATIVE

(71) Applicant: Jiangsu Hengrui Medicine Co., Ltd., Jiangsu (CN)

(72) Inventors: Bing Liu, Jiangsu (CN); Lin Bian, Jiangsu (CN); Xiaohui Gao, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 16/461,336

(22) PCT Filed: Nov. 22, 2017

(86) PCT No.: PCT/CN2017/112237
§ 371 (c)(1),
(2) Date: May 15, 2019

(87) PCT Pub. No.: WO2018/095320
PCT Pub. Date: May 31, 2018

(65) Prior Publication Data
US 2019/0308972 A1 Oct. 10, 2019

(30) Foreign Application Priority Data
Nov. 23, 2016 (CN) .......................... 2016 1 1035019

(51) Int. Cl.
| | | |
|---|---|---|
| *C07D 487/04* | (2006.01) | |
| *C07D 471/04* | (2006.01) | |
| *A61K 31/519* | (2006.01) | |
| *A61P 29/00* | (2006.01) | |
| *A61P 19/02* | (2006.01) | |

(52) U.S. Cl.
CPC ......... *C07D 471/04* (2013.01); *C07D 487/04* (2013.01); *A61K 31/519* (2013.01); *A61P 19/02* (2018.01); *A61P 29/00* (2018.01); *Y02P 20/55* (2015.11)

(58) Field of Classification Search
CPC .. C07D 487/04; C07D 471/04; A61K 31/518; A61K 31/519
USPC ........................................ 544/280; 514/265.1
See application file for complete search history.

(56) References Cited

U.S. PATENT DOCUMENTS

| | | | |
|---|---|---|---|
| 9,422,300 B2 * | 8/2016 | Sun ......................... | A61P 29/00 |
| 9,527,851 B2 * | 12/2016 | Zhang ..................... | A61P 25/28 |
| 2014/0336207 A1 * | 11/2014 | Zhang ..................... | A61P 19/00 514/265.1 |
| 2016/0102098 A1 * | 4/2016 | Sun ......................... | A61P 37/00 514/265.1 |

FOREIGN PATENT DOCUMENTS

| | | |
|---|---|---|
| CN | 102510865 | 6/2012 |
| CN | 103415520 | 11/2013 |
| CN | 104470927 | 3/2015 |
| WO | WO 2001042246 | 6/2001 |
| WO | WO 2002000661 | 1/2002 |
| WO | WO 2008089636 | 7/2008 |
| WO | WO 2009054941 | 4/2009 |
| WO | WO 2011013785 | 2/2011 |
| WO | WO2012058645 | 5/2012 |
| WO | WO 2013091539 | 6/2013 |
| WO | WO 2014194741 | 12/2014 |

OTHER PUBLICATIONS

International Search Report and Written Opinion in International Application No. PCT/CN2017/112237, dated Feb. 26, 2018, 10 pages.

* cited by examiner

*Primary Examiner* — Venkataraman Balasubramanian
(74) *Attorney, Agent, or Firm* — Fish & Richardson P.C.

(57) ABSTRACT

Disclosed are an intermediate of a pyrrolo six-membered heteroaromatic ring derivative as a JAK inhibitor and a preparation method therefor, and a method for preparing a pyrrolo six-membered heteroaromatic ring derivative using the intermediate. The method improves the reaction yield, is simple and easy to operate and control, and is conducive to expanded industrial production.

12 Claims, No Drawings

PREPARATION METHOD FOR AND INTERMEDIATE OF PYRROLO SIX-MEMBERED HETEROAROMATIC RING DERIVATIVE

CROSS-REFERENCE TO RELATED APPLICATIONS

This application is a National Stage Application under 35 U.S.C. §371 and claims the benefit of International Application No. PCT/CN2017/112237, filed Nov. 22, 2017, which claims priority to CN Application No. 201611035019.5, filed Nov. 23, 2016. The disclosures of the foregoing applications are hereby incorporated by reference in their entirety.

FIELD OF THE INVENTION

The present invention relates to a method for preparing a pyrrolo six-membered heteroaromatic ring derivative and a pharmaceutically acceptable salt thereof, and an intermediate in the preparation process and a method for preparing the same. The pyrrolo six-membered heteroaromatic ring derivative as a JAK inhibitor can be used in the preparation of a medicament for treating myeloproliferative neoplasms and/or leukemia.

BACKGROUND OF THE INVENTION

JAK protein kinase inhibitors, particularly JAK3 protein kinase inhibitors, can impede activation of T-cell, and prevent graft rejection after transplantation. These drugs can provide a therapeutic benefit for other autoimmune diseases as well. As an important protein kinase, JAK3 can also adjust the function of lymphocytes, macrophages, and mast cells. JAK3 inhibitors are expected to be involved in the treatment or prevention of a variety of diseases associated with the function of lymphocytes, macrophages, or mast cells. Some studies found that in patients suffering from marrow fibrosis diseases, JAK2 kinase mutation was produced in more than 50% of patients in vivo, and the increase of the risk of disease-related symptoms such as anemia, splenomegaly, and the transformation to acute myeloid leukemia (AML), was closely associated with the increased activity due to JAK2 gene mutation and abnormal activity of JAK-STAT signaling pathway. Meanwhile, JAK2 activity was increased abnormally in a variety of solid tumors and hematological tumors (glioblastoma, breast cancer, multiple myeloma, prostate cancer, AML, etc.). Therefore, the development of a selective inhibitor of JAK2 for myeloproliferative neoplasms and leukemia therapy has a great medical value and market potential (a selective inhibitor of JAK2 named Ruxolitinib (INCB-018424), developed by INCYTE Corp in cooperation with NOVARTIS, has been approved by the FDA and appeared on the market successfully).

Currently, a series of pyrrolo six-membered heteroaromatic ring derivative JAK inhibitors have been disclosed in, for example, WO2001042246, WO2002000661, WO2009054941, WO2011013785, WO2013091539A1, WO2014194741A1, etc. Among them, WO2013091539A1 discloses a method for preparing a pyrrolo six-membered heteroaromatic ring derivative (compound 34) as follows:

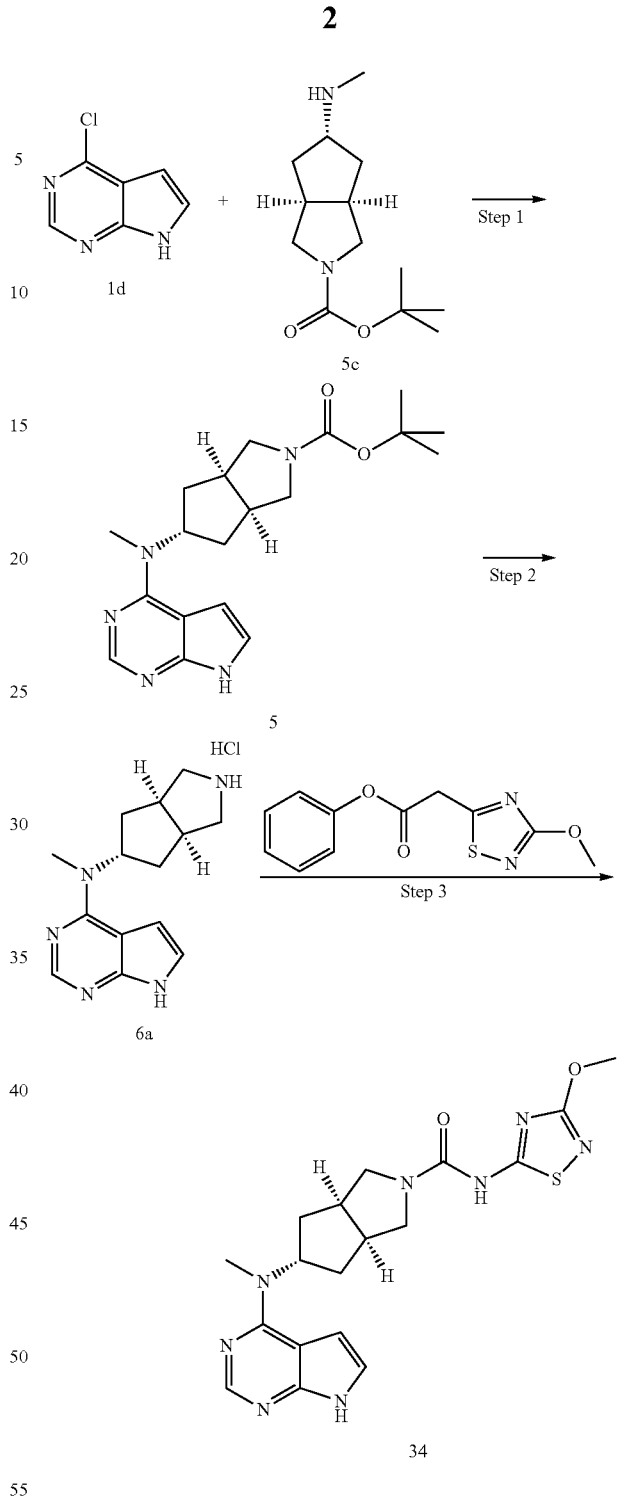

There is a bare imino group present in the structure of the starting material compound 1d of this method, which can react with the chlorine atom on the self six-membered ring to produce a by-product. The yield of intermediate 5 is merely 5.0%, and the reaction time is up to 48 hours. The final product 34 is prepared from a hydrochloride of a compound of formula (III) and a compound of formula (C), and the post-treatment is carried out by column chromatography, and the yield is merely 25.9%. This method is not conducive to industrial production. Therefore, it is necessary to improve the existing preparation method.

SUMMARY OF THE INVENTION

The technical problem to be solved by the present invention is to provide a method and an intermediate for preparing a compound of formula (IV). The yield of the intermediate is improved by changing starting materials, and the final product is prepared from a free base of formula (III). This method is simple and controllable, the reactants such as starting materials are simple and easy to purchase, the reaction conditions are simple and controllable, the post-treatment process is simple, and the reaction yield is significantly improved. This method is conducive to industrial production.

The technical solution of the present invention is as follows:

The present invention provides a compound of formula (I) or a stereoisomer thereof:

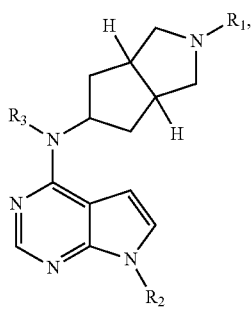

(I)

wherein, $R_1$ is hydrogen or an amino protecting group:

$R_2$ is an amino protecting group;

$R_3$ is selected from the group consisting of hydrogen, $C_{1-6}$ alkyl and an amino protecting group;

the amino protecting group is preferably selected from the group consisting of alkoxycarbonyl amino protecting group, acyl amino protecting group, sulfonyl amino protecting group and alkyl amino protecting group, the alkoxycarbonyl amino protecting group is selected from the group consisting of benzyloxycarbonyl (Cbz), tert-butoxycarbonyl (Boc), fluorenylmethoxycarbonyl (Fmoc), allyloxycarbonyl (Alloc), trimethylsilylethoxycarbonyl (Teoc), methoxycarbonyl and ethoxycarbonyl, the acyl amino protecting group is selected from the group consisting of phthalyl (Pht), trifluoroacetyl (Tfa), pivaloyl, benzoyl, formyl and acetyl;

the sulfonyl amino protecting group is selected from the group consisting of p-toluenesulfonyl (Tos or Ts), o-nitrobenzenesulfonyl (o-Ns) and p-nitrobenzenesulfonyl (p-Ns); and the alkyl amino protecting group is selected from the group consisting of trityl (Trt), 2,4-dimethoxybenzyl (Dmb), p-methoxybenzyl (PMB) and benzyl (Bn).

Preferably, wherein, $R_1$ is an alkoxycarbonyl amino protecting group, and the alkoxycarbonyl amino protecting group is preferably selected from the group consisting of benzyloxycarbonyl (Cbz), tert-butoxycarbonyl (Boc), fluorenylmethoxycarbonyl (Fmoc) and allyloxycarbonyl (Alloc), and more preferably tert-butoxycarbonyl (Boc):

$R_2$ is a sulfonyl amino protecting group, and the sulfonyl amino protecting group is preferably selected from the group consisting of p-toluenesulfonyl (Tos or Ts), o-nitrobenzenesulfonyl (o-Ns) and p-nitrobenzenesulfonyl (p-Ns), and more preferably p-toluenesulfonyl (Ts); and $R_3$ is selected from the group consisting of hydrogen and methyl.

In a preferred embodiment of the present invention, the present invention provides a compound of formula (Ia) or a stereoisomer thereof.

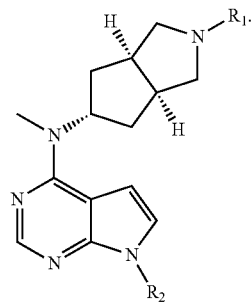

(Ia)

In a preferred embodiment of the present invention, the present invention provides a compound of formula (Ib) or a stereoisomer thereof,

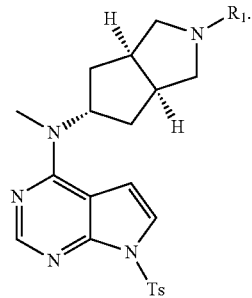

(Ib)

In a preferred embodiment of the present invention, the present invention provides a compound of formula (Ic) or a stereoisomer thereof,

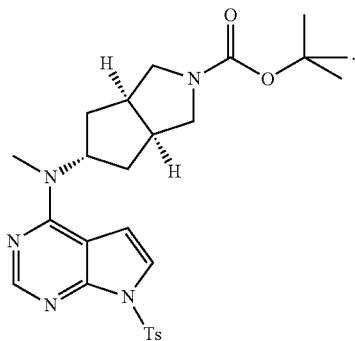

(Ic)

The present invention further relates to a method for preparing the compound of formula (I), characterized in that the method is a step of reacting a compound of formula (A) with a compound of formula (B),

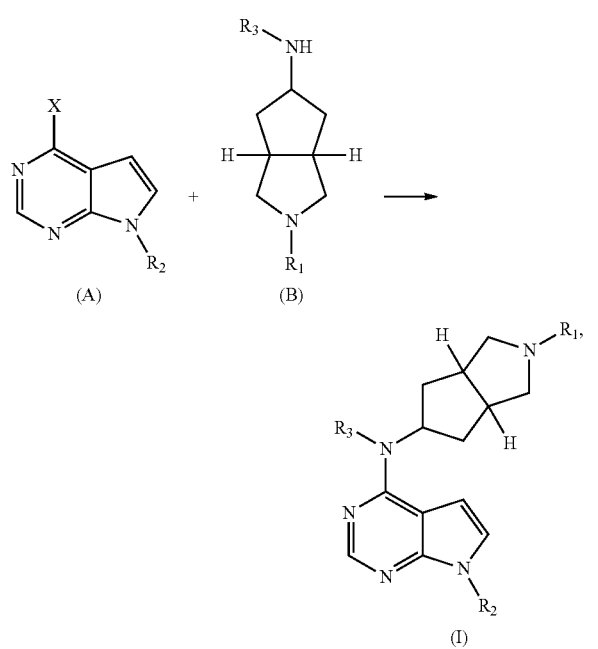

(A) + (B) → (I)

wherein,

X is halogen, and the halogen is selected from the group consisting of the atoms of fluorine, chlorine, bromine and iodine.

Preferably, the method is a reaction of a compound of formula (A) with a compound of formula (B1) to obtain a compound of formula (Ia),

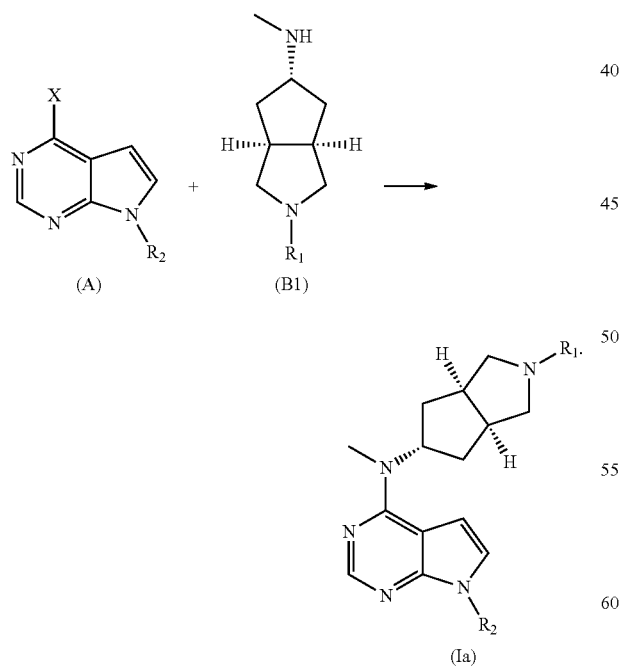

(A) + (B1) → (Ia)

Preferably, the method is a reaction of a compound of formula (A1) with a compound of formula (B1) to obtain a compound of formula (Ib),

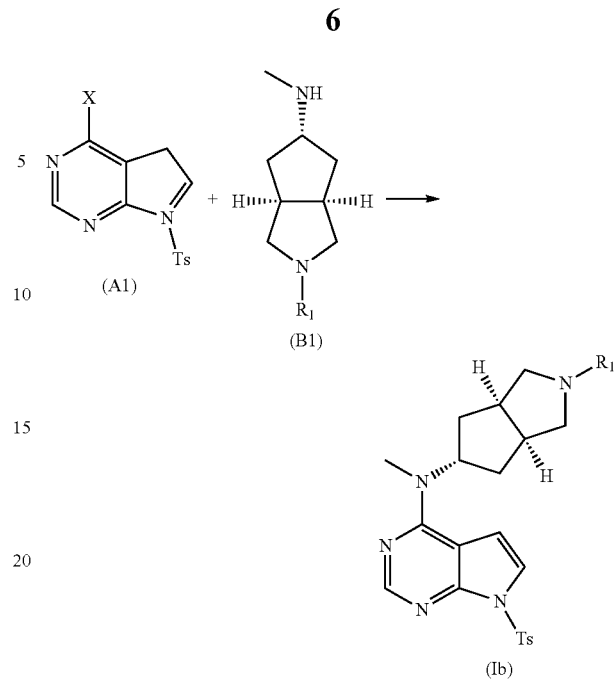

(A1) + (B1) → (Ib)

Further preferably, the method is a reaction of a compound of formula (A2) with a compound of formula (B2) to obtain a compound of formula (Ic),

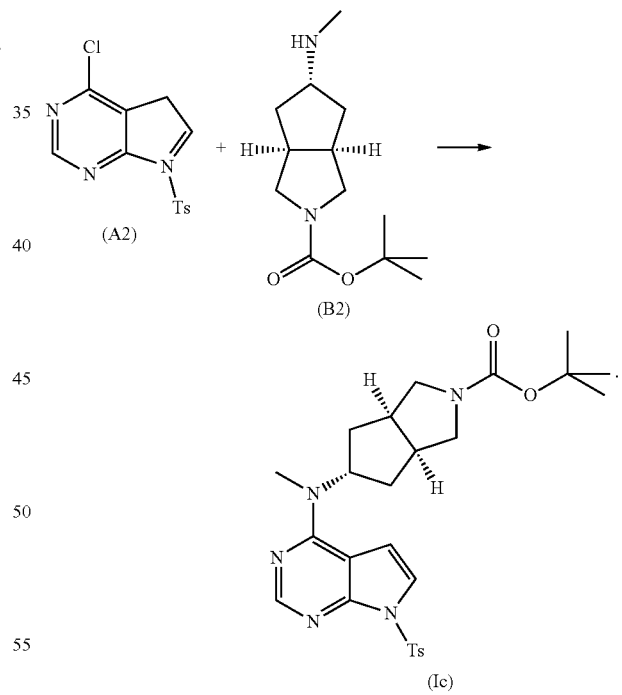

(A2) + (B2) → (Ic)

In the above schemes, the reaction is carried out in the presence of an organic solvent and a base. After completion of the reaction, water is added to precipitate a crystal. The mixture is filtrated, and the filter cake is dissolved in a halohydrocarbon solvent. Two phases were separated, and the resulting crude product is recrystallized to obtain the product. The reaction temperature is from 30° C. to the boiling point of the solvent, and preferably 100° C. The organic solvent includes, but is not limited to, one or more of amide, alcohol, ether, ketone and nitrile, preferably N,N-dimethylacetamide, N,N-dimethylformamide, tetrahydrofuran, acetone, acetonitrile, methanol, ethanol, dimethyl sulfoxide and 1,4-dioxane, and more preferably N,N-dimethylformamide (DMF). The base includes, but is not limited to, an organic base and an inorganic base. The organic base includes, but is not limited to, triethylamine, N,N-diisopropylethylamine, n-butyllithium, potassium tert-butoxide, sodium tert-butoxide, 1,8-diazabicycloundec-7-ene, pyridine and 4-dimethylaminopyridine. The inorganic base includes, but is not limited to, sodium hydride, sodium carbonate, potassium carbonate, sodium bicarbonate, potassium phosphate, lithium carbonate, lithium hydrogen phosphate, potassium bicarbonate and cesium carbonate, and preferably potassium carbonate. The halohydrocarbon solvent is preferably dichloromethane. The recrystallization method can be carried out by a conventional recrystallization process. For example, the starting compound can be dissolved in an organic solvent by heating, then cooled slowly to precipitate a crystal, and the mixture is filtrated after the completion of crystallization and dried to obtain the desired crystal. Alternatively, the target product can be obtained by a good solvent/anti-solvent recrystallization method (good solvent/anti-solvent method).

The present invention also relates to a compound of formula (I') or a stereoisomer thereof:

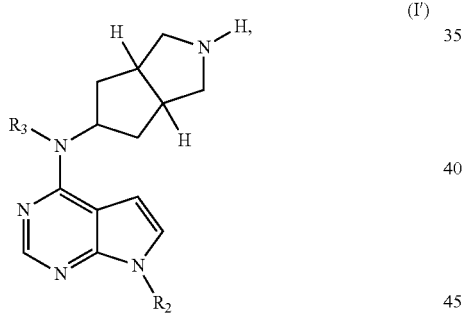

wherein, $R_2$ and $R_3$ are as defined in formula (I).

Preferably, the present invention provides a compound of formula (I'-1) or a stereoisomer thereof,

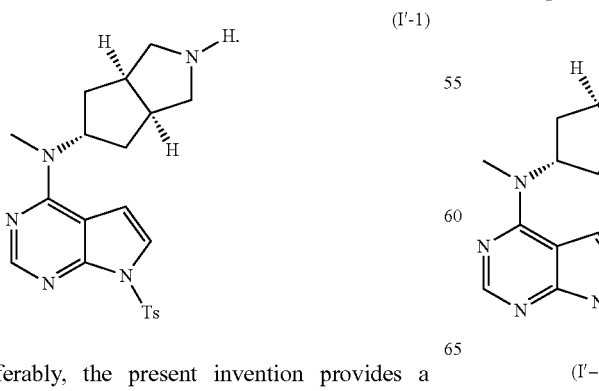

Further preferably, the present invention provides a method for preparing a compound of formula (IV), characterized in that the method comprises a step of obtaining the compound of formula (IV) from a compound of formula (I') by an one-step reaction or multi-step reaction,

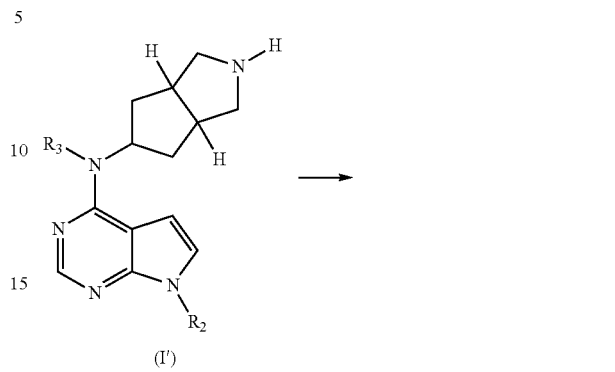

More preferably, the present invention provides a method for preparing the compound of formula (IV), characterized in that the method consists in obtaining the compound of formula (IV) from a compound of formula (I'-1) by an one-step reaction or multi-step reaction, -continued

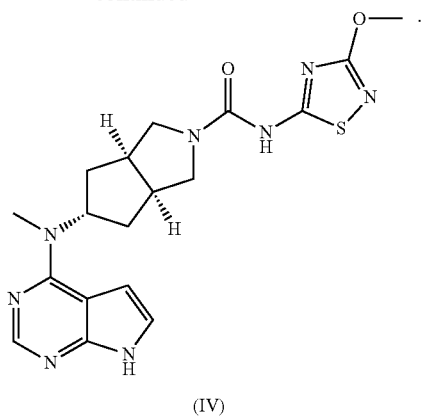

(IV)

Preferably, the compound of formula (I'-1) and phenyl (3-methoxy-1,2,4-thiadiazol-5-yl)carbamate are subjected to a substitution reaction to obtain the compound of formula (IV).

Further preferably, the compound of formula (I'-1) and phenyl (3-methoxy-1,2,4-thiadiazol-5-yl)carbamate are reacted in an organic solvent, and then a crystal is precipitated, filtrated and dried to obtain the target compound of formula (IV).

The present invention also relates to a method for preparing the compound of formula (IV), characterized in that the method comprises a step of obtaining the compound of formula (IV) from a compound of formula (Ic) by an one-step reaction or multi-step reaction, Preferably, the compound of formula (Ic) and phenyl (3-methoxy-1,2,4-thiadiazol-5-yl)carbamate are subjected to a substitution reaction to obtain the compound of formula (IV).

Further preferably, the compound of formula (Ic), phenyl (3-methoxy-1,2,4-thiadiazol-5-yl)carbamate and a base are reacted in an organic solvent, and then a crystal is precipitated, filtrated and dried to obtain the target compound of formula (IV).

In the above schemes, the organic solvent includes, but is not limited to, one or to more of amide, alcohol, ether, ester, halohydrocarbon, aliphatic hydrocarbon, ketone and nitrile, preferably n-butane, n-hexane, N,N-dimethylacetamide, N,N-dimethylformamide, tetrahydrofuran, dichloromethane, chloroform, ethyl acetate, acetone, acetonitrile, methanol, ethanol, toluene, dimethyl sulfoxide, 1,4-dioxane and methyl ether, and more preferably tetrahydrofuran. The base includes, but is not limited to, an organic base and an inorganic base. The organic base includes, but is not limited to, triethylamine, N,N-diisopropylethylamine, n-butyllithium, potassium tert-butoxide, sodium tert-butoxide, 1,8-diazabicycloundec-7-ene, pyridine and 4-dimethylaminopyridine. The inorganic base includes, but is not limited to, sodium hydride, sodium carbonate, potassium carbonate, sodium bicarbonate, potassium phosphate, lithium carbonate, lithium hydrogen phosphate, potassium bicarbonate and cesium carbonate. The base is preferably triethylamine. The reaction temperature is from 15° C. to the boiling point of the solvent, and preferably from 50° C. to the boiling point of the solvent.

The present invention also relates to a method for preparing the compound of formula (IV), characterized in that the method comprises a step of reacting a compound of formula (III) with a compound of formula (C) to obtain the compound of formula (IV),

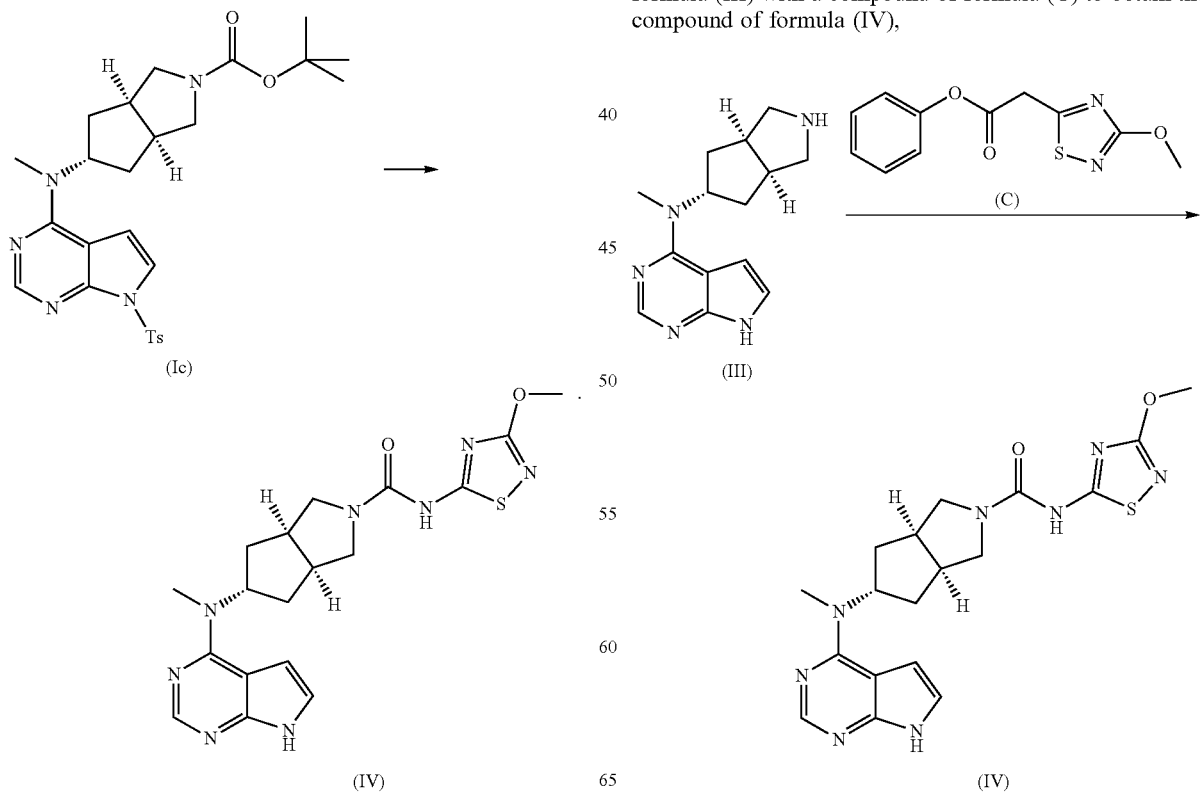

Preferably, the free base compound of formula (III) and phenyl (3-methoxy-1,2,4-thiadiazol-5-yl)carbamate are subjected to a substitution reaction to obtain the compound of formula (IV).

Further preferably, the free base compound of formula (III), phenyl (3-methoxy-1,2,4-thiadiazol-5-yl)carbamate and a base are reacted in an organic solvent, and then a crystal is precipitated, filtrated and dried to obtain the target compound of formula (IV).

More preferably, the organic solvent includes, but is not limited to, one or more of amide, alcohol, ether, ester, halohydrocarbon, aliphatic hydrocarbon, ketone and nitrile, preferably n-butane, n-hexane, N,N-dimethylacetamide, N,N-dimethylformamide, tetrahydrofuran, dichloromethane, chloroform, ethyl acetate, acetone, acetonitrile, methanol, ethanol, toluene, dimethyl sulfoxide, 1,4-dioxane and methyl ether, and more preferably tetrahydrofuran. The base includes, but is not limited to, an organic base and an inorganic base. The organic base includes, but is not limited to, triethylamine, N,N-diisopropylethylamine, n-butyllithium, potassium tert-butoxide, sodium tert-butoxide, 1,8-diazabicycloundec-7-ene, pyridine and 4-dimethylaminopyridine. The inorganic base includes, but is not limited to, sodium hydride, sodium carbonate, potassium carbonate, sodium bicarbonate, potassium phosphate, lithium carbonate, lithium hydrogen phosphate, potassium bicarbonate and cesium carbonate. The base is preferably triethylamine. The reaction temperature is from 15° C. to the boiling point of the solvent, and preferably from 50° C. to the boiling point of the solvent. The present invention further relates to a method for preparing the compound of formula (III), characterized by removing the amino protecting groups of a compound of formula (Ia) to obtain the compound of formula (III).

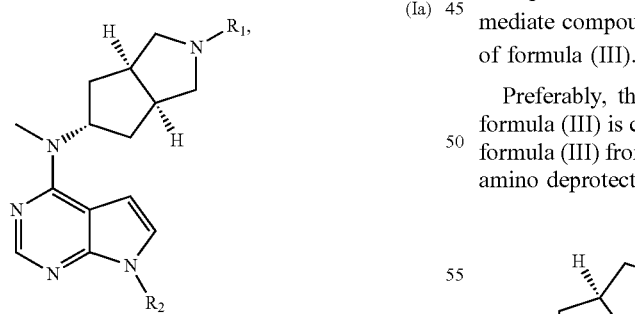

wherein $R_1$ and $R_2$ are as defined in formula (I).

Preferably, the deprotection reaction of the above scheme is a two-step deprotection reaction.

More preferably, the deprotection reaction of the above scheme is an one-step deprotection reaction.

In the above scheme, the two-step amino deprotection reaction comprises the steps of,

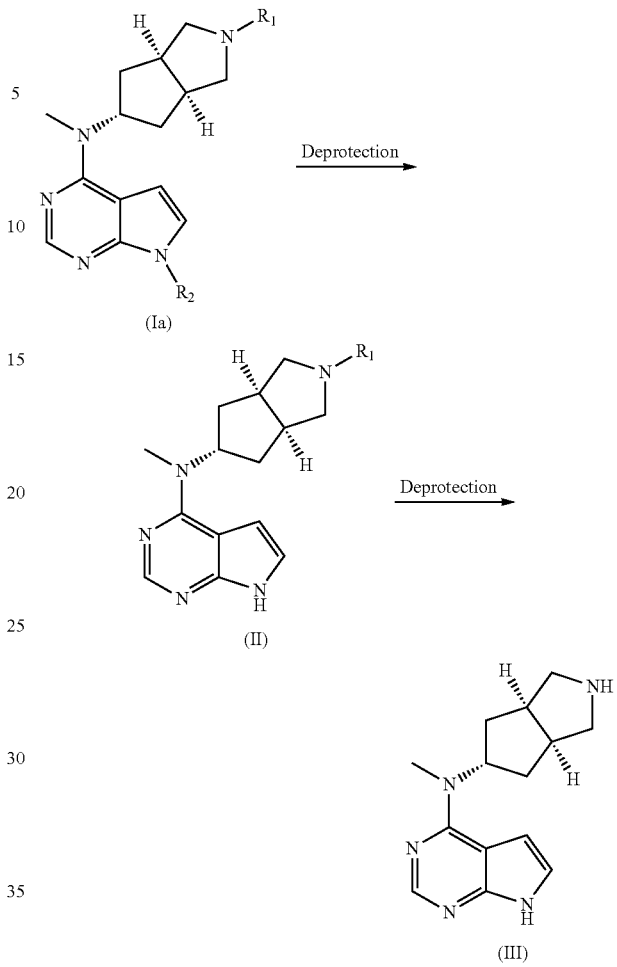

step 1, removing an amino protecting group of the intermediate compound of formula (Ia) to obtain an intermediate compound of formula (II);

step 2, removing an amino protecting group of the intermediate compound of formula (II) to obtain the compound of formula (III).

Preferably, the method for preparing the compound of formula (III) is characterized by obtaining the compound of formula (III) from a compound of formula (Ib) by a two-step amino deprotection reaction,

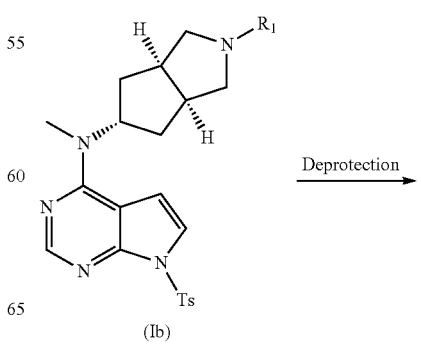

-continued

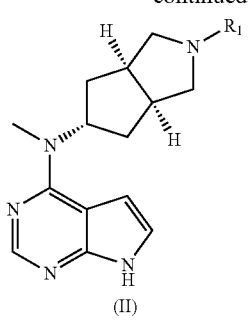

(II)

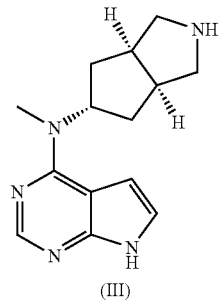

(III)

Further preferably, the method for preparing the compound of formula (III) is characterized by obtaining the compound of formula (III) from a compound of formula (Ic) by a two-step amino deprotection reaction,

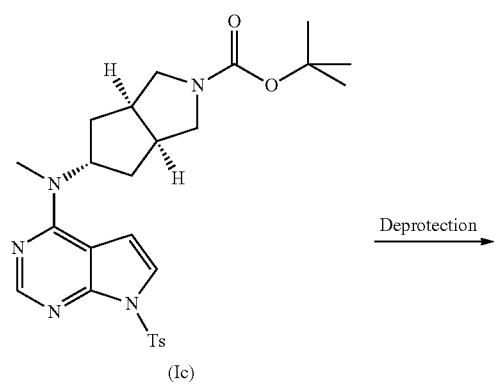

(Ic)

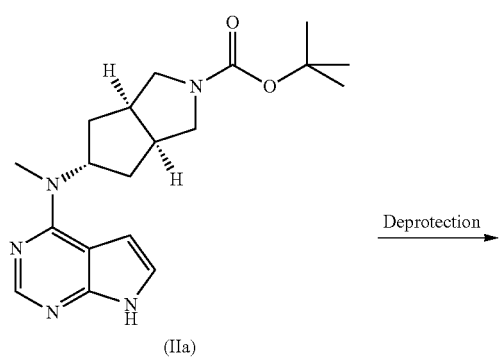

(IIa)

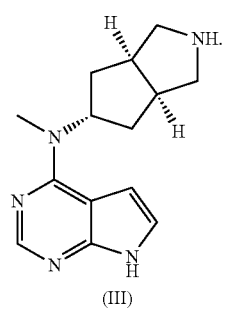

(III)

More preferably,

The intermediate of formula (Ia) in step 1 is reacted with a base in an organic solvent under heating to remove an amino protecting group. The reaction solution is extracted, and the resulting crude product is pulped in a mixed solvent of an ester and an ether to obtain the target intermediate of formula (II). The heating temperature is from 50° C. to the boiling point of the solvent, and preferably 70° C. The organic solvent includes, but is not limited to, one or more of amide, alcohol, ether, ketone and nitrile, preferably N,N-dimethylacetamide, N,N-dimethylformamide, tetrahydrofuran, acetone, acetonitrile and methanol, and more preferably N,N-dimethylacetamide. The base includes, but is not limited to, an organic base and an inorganic base. The organic base includes, but is not limited to, lithium diisopropylamide (LDA), n-butyllithium, sodium ethoxide, sodium methoxide, sodium ethoxide, potassium ethoxide and sodium tert-butoxide. The inorganic base includes, but is not limited to, sodium hydroxide, potassium hydroxide, sodium ethoxide, sodium methoxide, sodium ethoxide, potassium ethoxide, sodium tert-butoxide, sodium hydroxide and potassium hydroxide, and preferably sodium hydroxide and potassium hydroxide.

More preferably,

The intermediate of formula (II) in step 2 is reacted with an acid in an organic solvent to remove an amino protecting group. The extracted water phase is added with a base to adjust the pH and precipitate a solid. The solid is filtrated, pulped, filtrated again and dried to obtain the target intermediate of formula (III). The organic solvent includes, but is not limited to, an alcohol, ketone, nitrile, a mixed solvent of an alcohol and a halohydrocarbon, a mixed solvent of an alcohol and an ether, a mixed solvent of an alcohol and an ester, a mixed solvent of a ketone and a halohydrocarbon, a mixed solvent of a ketone and an ether, a mixed solvent of a ketone and an ester, a mixed solvent of a nitrile and a halohydrocarbon, a mixed solvent of a nitrile and an ether, and a mixed solvent of a nitrile and an ester, preferably methanol, ethanol, acetone, acetonitrile, methanol/dichloromethane, methanol/ethyl acetate, methanol/1,4-dioxane, acetone/dichloromethane, acetone/ethyl acetate, acetone/1,4-dioxane, acetonitrile/dichloromethane, acetonitrile/ethyl acetate and acetonitrile/1,4-dioxane, and more preferably methanol/dichloromethane. The acid is selected from the group consisting of formic acid, acetic acid, methanesulfonic acid, p-toluenesulfonic acid, isethionic acid, hydrochloric acid and trifluoroacetic acid, and preferably hydrochloric acid. The base is selected from metal hydroxide, preferably sodium hydroxide or potassium hydroxide.

Most preferably, wherein, $R_1$ is an alkoxycarbonyl amino protecting group, and the alkoxycarbonyl amino protecting group is preferably selected from the group consisting of benzyloxycarbonyl (Cbz), tert-butoxycarbonyl (Boc), fluorenylmethoxy carbonyl (Fmoc) and allyloxycarbonyl (Alloc), and more preferably tert-butoxycarbonyl (Boc):

R₂ is a sulfonyl amino protecting group, and the sulfonyl amino protecting group is preferably selected from the group consisting of p-toluenesulfonyl (Tos or Ts), o-nitrobenzenesulfonyl (o-Ns) and p-nitrobenzenesulfonyl (p-Ns), and more preferably p-toluenesulfonyl (Ts).

In the above scheme, the one-step amino deprotection reaction comprises a step of simultaneously removing the two amino protecting groups of the compound of formula (Ia) by an one-step reaction to obtain the compound of formula (III).

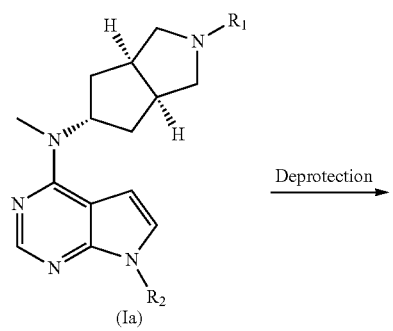

(Ia)

Preferably, the two amino protecting groups of the compound of formula (Ib) are simultaneously removed by an one-step reaction to obtain the compound of formula (III),

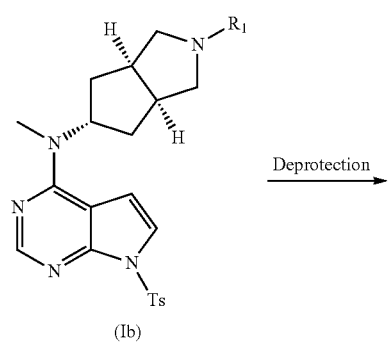

(Ib)

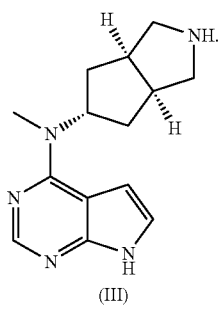

(III)

Preferably, the two amino protecting groups of the compound of formula (Ic) are simultaneously removed by an one-step reaction to obtain the compound of formula

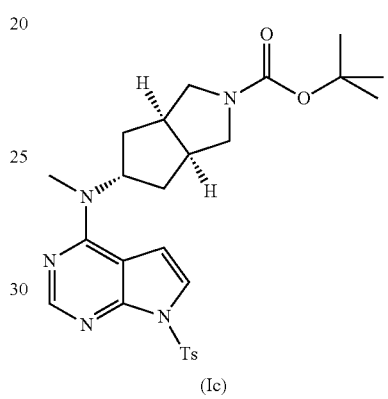

(Ic)

(III)

Further preferably, wherein,

R₁ is an alkoxycarbonyl amino protecting group, and the alkoxycarbonyl amino protecting group is preferably selected from the group consisting of benzyloxycarbonyl (Cbz), tert-butoxycarbonyl (Boc), fluorenylmethoxycarbonyl (Fmoc) and allyloxycarbonyl (Alloc), and more preferably tert-butoxycarbonyl (Boc);

R₂ is a sulfonyl amino protecting group, and the sulfonyl amino protecting group is preferably selected from the group consisting of p-toluenesulfonyl (Tos or Ts), o-nitrobenzenesulfonyl (o-Ns) and p-nitrobenzenesulfonyl (p-Ns), and more preferably p-toluenesulfonyl (Ts).

In one aspect, the present invention relates to a method for preparing the compound of formula (IV), characterized in that the method comprises the following steps of,

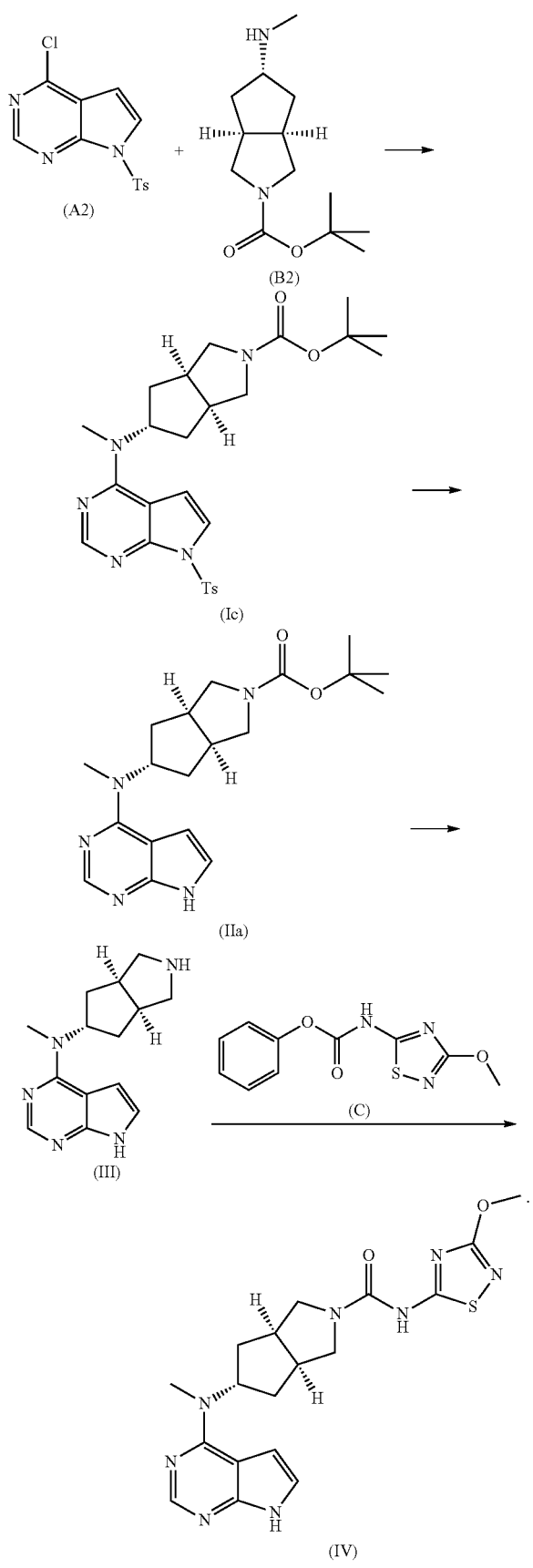

Step 1, Preparation of Intermediate Ic

Compounds A2 and B2 are dissolved in an organic solvent under the protection of inert gas, and heated to react after adding a base. After completion of the reaction, the reaction solution is cooled to room temperature, added with water and filtrated. The solid is dissolved in a halohydrocarbon solvent, and then extracted. The solution is dried, and then concentrated under reduced pressure to obtain the intermediate Ic. The organic solvent includes, but is not limited to, one or more of amide, alcohol, ether, ketone and nitrile, preferably n-butane, n-hexane, N,N-dimethylacetamide, N,N-dimethylformamide, tetrahydrofuran, acetone, acetonitrile, methanol, ethanol, dimethyl sulfoxide and 1,4-dioxane, and more preferably N,N-dimethylformamide. The base includes, but is not limited to, an organic base and an inorganic base. The organic base includes, but is not limited to, triethylamine, N,N-diisopropylethylamine, n-butyl-lithium potassium tert-butoxide, sodium tert-butoxide, 1,8-diazabicycloundec-7-ene, pyridine and 4-dimethylaminopyridine. The inorganic base includes, but is not limited to, sodium hydride, sodium carbonate, potassium carbonate, sodium bicarbonate, potassium phosphate, lithium carbonate, lithium hydrogen phosphate, potassium bicarbonate and cesium carbonate, and preferably potassium carbonate. The halohydrocarbon solvent is preferably dichloromethane.

Step 2, Preparation of intermediate IIa

The intermediate Ic is dissolved in an organic solvent, added with a base and water under stirring, and heated to react. After completion of the reaction, the reaction solution is cooled to room temperature, added with water and a halohydrocarbon solvent, and extracted. The reaction solution is dried, and concentrated under reduced pressure to obtain the intermediate IIa. The organic solvent includes, but is not limited to, one or more of amide, alcohol, ether, ketone and nitrile, preferably N,N-dimethylacetamide, N,N-dimethylformamide, tetrahydrofuran, acetone, acetonitrile and methanol, and more preferably N,N-dimethylacetamide. The base includes, but is not limited to, an organic base and an inorganic base. The organic base includes, but is not limited to, lithium diisopropylamide (LDA), n-butyllithium, sodium ethoxide, sodium methoxide, sodium ethoxide, potassium ethoxide and sodium tert-butoxide. The inorganic base includes, but is not limited to, sodium hydroxide and potassium hydroxide, and preferably sodium hydroxide or potassium hydroxide. The halohydrocarbon solvent is preferably dichloromethane.

Step 3, Preparation of Intermediate III

The intermediate IIa is dissolved in an organic solvent, added dropwise with an acid at low temperature, and stirred to react at room temperature. After completion of the reaction, the reaction solution is concentrated, added with water to dissolve, and added with a halohydrocarbon solvent to extract. The water phase is added with a base to adjust the pH to alkaline and precipitate a solid. The solid is filtrated and dried to obtain the intermediate III.

The organic solvent includes, but is not limited to, an alcohol, ketone, nitrile, a mixed solvent of an alcohol and a halohydrocarbon, a mixed solvent of an alcohol and an ether, a mixed solvent of an alcohol and an ester, a mixed solvent of a ketone and a halohydrocarbon, a mixed solvent of a ketone and an ether, a mixed solvent of a ketone and an ester, a mixed solvent of a nitrile and a halohydrocarbon, a mixed solvent of a nitrile and an ether, and a mixed solvent of a nitrile and an ester, preferably methanol, ethanol, acetone, acetonitrile, methanol/dichloromethane, methanol/ethyl acetate, methanol/1,4-dioxane, acetone/dichloromethane, acetone/ethyl acetate, acetone/1,4-dioxane, acetonitrile/dichloromethane, acetonitrile/ethyl acetate and acetonitrile/1,4-dioxane, and more preferably methanol/dichloromethane. The acid is selected from the group consisting of formic acid, acetic acid, methanesulfonic acid, p-toluenesulfonic acid, isethionic acid, hydrochloric acid and trifluoroacetic acid, and preferably hydrochloric acid. The base is preferably an inorganic base, and the inorganic base is preferably a metal hydroxide, such as sodium hydroxide and potassium hydroxide. The pH to alkaline is preferably from 8 to 11, and more preferably from 9 to 10.

Step 4, Preparation of Product IV

The intermediate III and compound C are added to an organic solvent, added with a base, and heated to react. After completion of the reaction, the reaction solution is cooled to precipitate a crystal, which is then filtrated and dried to obtain the product IV. The organic solvent includes, but is not limited to, an amide, alcohol, ether, ester, halohydrocarbon, aliphatic hydrocarbon, ketone and nitrile, preferably n-butane, n-hexane, N,N-dimethylacetamide, N,N-dimethylformamide, tetrahydrofuran, dichloromethane, chloroform, ethyl acetate, acetone, acetonitrile, methanol, ethanol, toluene, dimethyl sulfoxide, 1,4-dioxane and methyl ether, and more preferably tetrahydrofuran. The base includes, but is not limited to, an organic base and an inorganic base. The organic base includes, but is not limited to, triethylamine, N,N-diisopropylethylamine, n-butyllithium, potassium tert-butoxide, sodium tert-butoxide, 1,8-diazabicycloundec-7-ene, pyridine and 4-dimethylaminopyridine. The inorganic base includes, but is not limited to, sodium hydride, sodium carbonate, potassium carbonate, sodium bicarbonate, potassium phosphate, lithium carbonate, lithium hydrogen phosphate, potassium bicarbonate and cesium carbonate. The base is preferably triethylamine.

In another aspect, the present invention relates to a method for preparing a pharmaceutically acceptable salt of the compound of formula (IV), comprising the steps in the above schemes, and a step of reacting the compound of formula (IV) with an acid to obtain a pharmaceutically acceptable salt thereof, wherein the acid is selected from the group consisting of an organic acid and an inorganic acid, and preferably an inorganic acid; the organic acid is selected from the group consisting of citric acid, acetic acid, trifluoroacetic acid, oxalic acid, tartaric acid, maleic acid fumaric acid, p-toluenesulfonic acid, benzenesulfonic acid and methanesulfonic acid; the inorganic acid is selected from the group consisting of hydrochloric acid, sulfuric acid and phosphoric acid, and preferably sulfuric acid.

DETAILED DESCRIPTION OF THE INVENTION

In the specification and claims of the present application, unless otherwise indicated the scientific and technical terms used herein have the meanings generally understood by a person skilled in the art. However, in order to understand the present invention better, definitions and explanations of some related terms are provided. In addition, when the definitions and explanations of the terms provided in the present application are inconsistent with the meanings generally understood by a person skilled in the art, the definitions and explanations of the terms provided in the present application shall prevail.

The term "protecting group" used in the present invention means that when a multifunctional organic compound is subjected to a reaction, in order to make the reaction occur only at a desired group and to prevent other groups from being affected, other groups are protected before the reaction and recovered after the reaction is completed. A reagent that protects a certain group is called a protecting group for the group. The basic principles for choosing a protecting group are as follows: the protection reaction and deprotection reaction are required to be mild and easy to operate, the reaction has a high yield and less side reactions, the product is easy to purify, and the reagents does not involve in other reactions and are cheap and easy to purchase, etc.

The term "amino protecting group" used in the present invention refers to a group capable of protecting an amino group from reactions. Conventional amino protecting groups include, but are not limited to: formate (prepared by the reaction of an amino group with chloroformate, diazocarboxylate or various carbonates), imine (prepared by the reaction of a primary amine with aromatic aldehyde, aromatic ketone or fatty ketone), alkoxycarbonyl (benzyloxycarbonyl (Cbz), tert-butoxycarbonyl (Boc), fluorenylmethoxycarbonyl (Fmoc), allyloxycarbonyl (Alloc), trimethylsilylethoxycarbonyl (Teoc), methoxycarbonyl and ethoxycarbonyl), acyl (prepared by the reaction of an amino group with acid chloride or anhydride, for example phthalyl (Pht), trifluoroacetyl (Tfa), pivaloyl, benzoyl, formyl and acetyl), sulfonyl (aromatic sulfonamide such as p-toluenesulfonyl (Tos or Ts), o-nitrobenzenesulfonyl (o-Ns) and p-nitrobenzenesulfonyl (p-Ns)), alkyl (trityl (Trt), 2,4-dimethoxybenzyl (Dmb), p-methoxybenzyl (PMB) and benzyl (Bn)) and the like, wherein "alkoxycarbonyl, acyl and sulfonyl" refer to R—O—C(O)—, R—C(O)— and R—S(O)$_2$—, respectively, wherein R can be hydrogen, alkyl or aryl.

The term "pulping" used in the present invention refers to a purification method utilizing the property that the solubility of a compound is poor in a solvent, while the solubility of impurities is good in the solvent. Pulping purification can remove color, change crystal form or remove small amounts of impurities.

The term "halogenated" used in the present invention refers to be substituted by a "halogen atom". The term "halogen atom" refers to fluorine, chlorine, bromine and iodine.

The term "$C_{1-6}$ alkyl" used in the present invention refers to a straight or branched alkyl containing 1 to 6 carbon atoms, including for example "$C_{1-4}$ alkyl", "$C_{1-3}$ alkyl" and the like. Its specific examples include, but are not limited to: methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc.

The term "cyano" used in the present invention refers to a —CN group.

The term "amide organic solvent" used in the present invention refers to a liquid compound in which a hydroxy group in a carboxyl group of a carboxylic acid molecule is substituted with an amino or a hydrocarbon amino group (—NHR or —NR$_2$). It can also be regarded as a liquid compound in which a hydrogen on a nitrogen atom of an ammonia or amine molecule is substituted with an acyl. Its specific examples include, but are not limited to: N,N-dimethylformamide or N,N-dimethylacetamide.

The term "ether solvent" used in the present invention refers to a chain compound or a cyclic compound having an ether bond —O— and having 1 to 10 carbon atoms. Its specific examples include, but are not limited to: propylene glycol methyl ether, tetrahydrofuran or 1,4-dioxane.

The term "ester solvent" used in the present invention refers to a combination of a lower organic acid having 1 to 4 carbon atoms and a lower alcohol having 1 to 6 carbon atoms. Its specific examples include, but are not limited to: ethyl acetate, isopropyl acetate or butyl acetate.

The term "alcohol solvent" used in the present invention refers to a group derived from the substitution of one or more hydrogen atom(s) on the "$C_{1-6}$ alkyl" with one or more "hydroxy(s)", wherein the "hydroxy" and "$C_{1-6}$ alkyl" are as defined above. Its specific examples include, but are not limited to: methanol, ethanol, n-propanol or 2-propanol.

The term "halohydrocarbon solvent" used in the present invention refers to a group derived from the substitution of one or more hydrogen atom(s) on the "$C_{1-6}$ alkyl" with one or more "halogen atom(s)", wherein the "halogen atom" and "$C_{1-6}$ alkyl" are as defined above. Its specific examples include, but are not limited to: chloromethane, dichloromethane, chloroform or carbon tetrachloride.

The term "ketone solvent" used in the present invention refers to a compound in which a carbonyl group (—C(O)—) is bonded to two hydrocarbon groups. Ketones can be classified into aliphatic ketones, alicyclic ketones, aromatic ketones, saturated ketones, and unsaturated ketones, depending on the hydrocarbon groups in the molecule. Its specific examples include, but are not limited to: acetone, methyl butanone or methyl isobutyl ketone.

The term "nitrile solvent" used in the present invention refers to a group derived from the substitution of one or more hydrogen atom(s) on the "$C_{1-6}$ alkyl" with one or more "cyano(s)", wherein the "cyano" and "$C_{1-6}$ alkyl" are as defined above. Its specific examples include, but are not limited to: acetonitrile or propionitrile.

The term "aliphatic hydrocarbon solvent" used in the present invention refers to a hydrocarbon having the basic properties of an aliphatic compound and having 1 to 10 carbon atoms, wherein the carbon atoms in the molecule are linked to a chain-like carbon frame in which the two ends are opened and do not form a ring, for example saturated aliphatic hydrocarbon, including alkane solvent. Its specific examples include, but are not limited to: n-butane, n-pentane, n-hexane or n-heptane. "Substituted" means that one or more hydrogen atoms in a group, preferably up to 5, and more preferably 1 to 3 hydrogen atoms, are each independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having a free hydrogen and carbon atoms having unsaturated (e.g., olefinic) bonds may be unstable.

The term "mixed solvent" used in the present invention refers to a solvent obtained by mixing one or more different kinds of organic solvents in a certain ratio, or a solvent obtained by mixing an organic solvent and water in a certain ratio. The mixed solvent is preferably a mixed solvent of an alcohol and a halohydrocarbon or a mixed solvent of an ester and an ether. The mixed solvent of an alcohol and a halohydrocarbon is preferably a mixed solvent of methanol and dichloromethane, the certain ratio may be volume ratio or mass ratio, the mass ratio is from 10:1 to 1:10, and preferably 1.6:1. The mixed solvent of an ester and an ether is preferably a mixed solvent of ethyl acetate and petroleum ether, the certain ratio may be volume ratio or mass ratio, the volume ratio is from 1:1 to 1:10, and preferably 1:4.

The term "acid" used in the present invention refers to an organic acid or an inorganic acid. "Organic acid" refers to a compound capable of accepting an electron pair according to the general theory of acid-base. The organic acid includes carboxylic acid, halogenated acid, hydroxy acid, keto acid, amino acid, sulfonic acid, sulfinic acid, sulfuric acid, phenolic acid and the like, and preferably sulfonic acid. The specific examples of sulfonic acid include, but are not limited to: formic acid, acetic acid, methanesulfonic acid, ethanesulfonic acid, dodecylbenzenesulfonic acid, benzenesulfonic acid, p-toluenesulfonic acid, trifluoromethanesulfonic acid, trifluoroacetic acid, isethionic acid and the like. "Inorganic acid" refers to an inorganic compound capable of dissociating a hydrogen ion. According to the composition, the inorganic acids can be classified into oxyacids, hydrogen acids, complex acids, mixed acids, super acids and the like, and the inorganic acid is preferably an oxyacid or hydrogen acid. The specific examples of oxyacid include, but are not limited to: carbonic acid, nitric acid, nitrous acid, hypochlorous acid, sulfuric acid, phosphoric acid and the like. The specific examples of hydrogen acid include, but are not limited to: hydrofluoric acid, hydrochloric acid, bromic acid, hydrogen sulfide and the like.

The term "base" used in the present invention refers to an organic base or an inorganic base. "Organic base" refers to a compound capable of giving an electron pair according to the general theory of acid-base. The organic bases are classified into amines, amides, alkali metal salts of an alcohol, alkyl lithium compounds, lithium amide compounds, nitrogen-containing heterocyclic compounds, organic bases providing a hydroxide, amino acids and the like. Its specific examples include, but are not limited to: dimethylamine, triethylamine, ethylenediamine, colchicine, sodium methoxide, sodium ethoxide, potassium ethoxide, sodium tert-butoxide, lithium tert-butoxide, n-butyl lithium, N,N-diisopropylethylamine, lithium diisopropylamide (LDA), pyrrolidine, pyridine, tetramethylammonium hydroxide, 1,8-diazabicycloundec-7-ene, 4-dimethylaminopyridine, lysine (Lys) and the like. "Inorganic base" refers to an inorganic compound capable of dissociating a hydroxide ion. According to the composition, the inorganic bases can be classified into metallides, metal hydroxides, ammonia or ammonia monohydrate, salts capable of dissociating a hydroxide ion and the like. Its specific examples include, but are not limited to: sodium hydride, lithium hydroxide, sodium hydroxide, potassium hydroxide, calcium hydroxide, magnesium hydroxide, sodium carbonate (soda ash), potassium carbonate, sodium bicarbonate (baking soda), potassium phosphate, lithium carbonate, lithium hydrogen phosphate, potassium bicarbonate, cesium carbonate and the like. Triethylamine, N,N-diisopropylethlamine, n-butyl lithium, potassium tert-butoxide, sodium tert-butoxide. The inorganic bases include, but are not limited to sodium hydride, sodium carbonate, potassium carbonate, sodium bicarbonate, potassium bicarbonate and cesium carbonate.

The term "pharmaceutically acceptable salt or medicinal salt" used in the present invention refers to a salt of the compound of the present invention, which is safe and effective in mammals and has the desired biological activity. The salt is specifically a compound formed by the compound of the present invention with an inorganic or organic acid. Its specific examples include, but are not limited to: citrate, hydrochloride, sulfate, hydrosulphate, phosphate, acetate, trifluoroacetate, oxalate, tartrate, maleate, fumarate, sulfonate, p-toluenesulfonate, benzenesulfonate, ethanesulfonate and methanesulfonate.

Advantageous Effects of the Present Invention

Compared with the prior art (WO2013091539A1, publication date: 27 Jun. 2013), the technical solution for preparing the compound of formula (IV) of the present invention has the following advantages:

(1) The present invention is different from the prior art in starting material. The nitrogen atom on the pyrrolyl group of the starting material the compound of formula (A) of the present invention is protected by a protecting group before reacting with the compound of formula (B), which can avoid the reaction between the bare amino on the five-membered ring of the compound of formula (A) and the halogen on the self six-membered ring, that is to say, thereby reducing side reactions that will cause the incomplete reaction between the compound of formula (A) and the compound of formula (B) and cause the decrease in product yield and increase in impurities.

(2) The prior art discloses a method for preparing the target product from a salt of the compound of formula (III), wherein triethylamine is firstly reacted with the hydrochloride salt of the compound of formula (III)

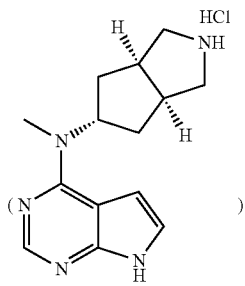

to dissociate the compound of formula (III), which is then reacted with the compound of formula (C) to obtain the target product. However, this method may leave too much compound of formula (III), and the reaction is incomplete. In the present invention, the protecting group of the compound of formula (I) is removed to obtain the free compound of formula (III)

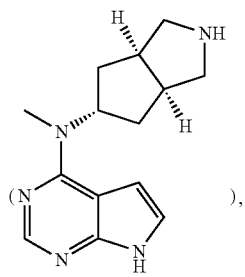

which is then reacted with the compound of formula (C) to obtain the target final product. The method of the present invention is easy to operate, and can improve the yield and purity of the product. Moreover, during the preparation of the compound of formula (III) in this method, the process of pH adjustment by adding a base can also remove the impurities, thus the resulting compound of formula (III) has a high purity.

(3) The reaction time is shortened. The reaction time of the first step for preparing the compound of formula (IIa) of the present invention is 2 hours, and the reaction time of the second step is 1 hour, while the reaction time of the first step disclosed in the prior art is 48 hours.

(4) The yield is improved. The yield of the first step of the present invention is 60-70%, the yield of the second step is 80-90%, and the total yield of the two steps is 48-63%, while the yield of the prior art is 5.0%; the yield of the final step of the present invention is 80-90%, while that of the prior art is 25.9%.

(5) The post-treatment process is simple. The post-treatment process of the present invention is cooling to precipitate a crystal, and simply washing to remove the impurities, thereby obtaining the target product, while that of the prior art is column chromatography separation and purification. The post-treatment process of the present invention is conducive to industrial production.

Preferred Embodiments

The present invention will be further described with reference to the following examples. The examples of the present invention are only used to illustrate the technical solutions of the present invention, and should not be considered as limiting the spirit and scope of the present invention.

In the examples of the present invention, the experiment methods that do not specify the specific conditions are generally conducted in accordance with conventional conditions, or in accordance with conditions recommended by the material or product manufacturers. The reagents without specific source are commercially available conventional reagents.

EXAMPLES

The structures of the compounds were identified by nuclear magnetic resonance (NMR) and/or mass spectrometry (MS). NMR shifts ($\delta$) were given in $10^{-6}$ (ppm). NMR was determined by a Bruker AVANCE-400 machine. The solvents for determination were deuterated-dimethyl sulfoxide (DMSO-$d_6$) and deuterated-chloroform (CDCl$_3$), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent high pressure liquid chromatograph and a Thermon UltiMate3000 high performance liquid chromatograph (Kromasil C18 250×4.6 mm column).

Preparation Example 1

The method for preparing the starting material the compound of formula (A2) is as follows:

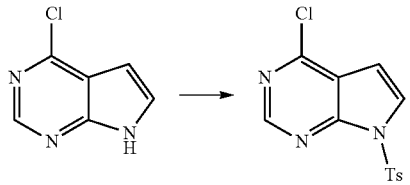 [SMILES: Clc1ncnc2[nH]ccc12 ; Cc1ccc(S(=O)(=O)n2ccc3c(Cl)ncnc32)cc1]

Preparation of 4-chloro-7-tosyl-7H-pyrrolo[2,3-d]pyrimidine

4-Chloro-7H-pyrrolo[2,3-d]pyrimidine (2 kg, 12.96 mol) and dichloromethane (40 L) were added to a reaction flask at room temperature, and stirred to dissolve. Triethylamine (3.88 kg, 38.4 mol) and 4-dimethylaminopyridine (157.6 g, 1.28 mol) were added successively, and stirred to dissolve. A solution of p-toluenesulfonyl chloride (2.6 kg, 13.6 mol) in dichloromethane (30 L) was added dropwise at 0° C., followed by stirring at room temperature for 30 minutes. After TLC showed that the reaction was completed, the reaction solution was washed with water (16 L×3). The organic phases were combined, dried over anhydrous sodium sulfate and filtrated. The filtrate was concentrated and dried under reduced pressure to obtain the title product (3.9 kg, yield 97.7%).

MS m/z (ESI): 309.0 [M+1]

$^1$H-NMR (400 MHz, CDCl$_3$) δ 8.77 (s, 1H), 8.10-8.08 (d, 2H), 7.79-7.78 (d, 1H), 7.34-7.32 (d, 2H), 6.72-6.71 (d, 1H), 2.41 (s, 3H).

Preparation Example 2

The starting material the compound of formula (B2) was prepared by the known methods disclosed in the Example 1 of WO2008089636A1 (publication date 31 Jul. 2008) and the Example 5 of WO2013091539A1 (publication date 27 Jun. 2013).

MS m/z (ESI): 241.5 [M+1]

$^1$H-NMR (400 MHz, CDCl$_3$) δ3.21 (m, 2H), 2.90-2.83 (m, 3H), 2.47-2.45 (m, 2H), 2.08 (s, 3H), 1.42-1.33 (m, 4H), 1.15 (s, 9H), 0.94 (s, 1H).

Preparation Example 3

The method for preparing the starting material the compound of formula (C) is as follows:

(1) Preparation of 1-(isothiocyanatomethyl)-4-methoxybenzene

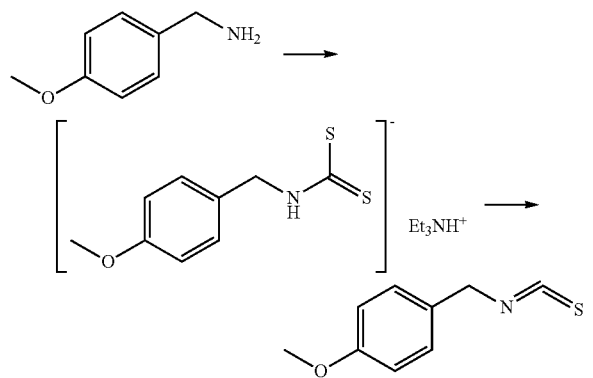

Methoxybenzylamine (14 kg), tetrahydrofuran (50 L) and triethylamine (26.8 kg) were added to a reactor, and stirred to dissolve. A solution of carbon disulfide (7.8 kg) in tetrahydrofuran (5 L) was added dropwise at 10-15° C. After completion of the dropwise addition, a solid was precipitated from the reaction solution, and the reaction was stirred at 10-20° C. for 30 minutes. A solution of p-toluenesulfonyl chloride (20.5 kg) in tetrahydrofuran (50 L) was added dropwise at 10-20° C. After completion of the dropwise addition, the reaction was stirred for 30 minutes. After TLC showed that the reaction was completed, the reaction solution was added with petroleum ether (30 L) and purified water (100) L) to extract, and two phases were separated. The organic phase was washed with dilute hydrochloric acid (40 L) until pH=4-5, and then washed with water (40 L) and brine (25 L) successively. Two phases were separated, the organic phase was dried over anhydrous sodium sulfate, filtrated and concentrated under reduced pressure to obtain the title product (21.2 kg, yield 116%/0).

(2) Preparation of 3-methoxy-N-(4-methoxybenzyl)-1,2,4-thiadiazol-5-amine

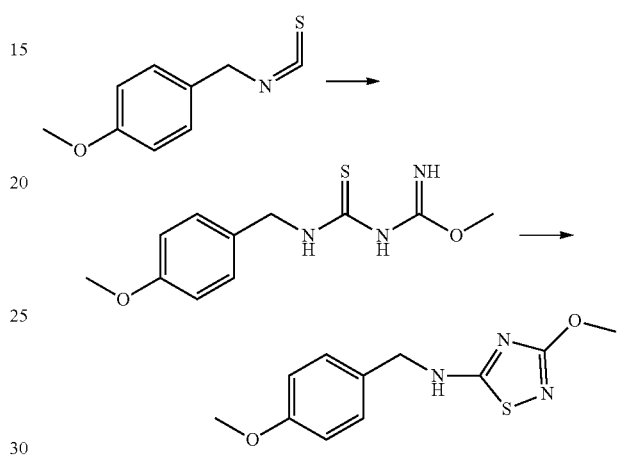

DMF (40 L), O-methylisourea sulfate (7.5 kg) and sodium bicarbonate (6 kg) were added to a reactor, and the reaction was stirred at 30-40° C. for 0.5 hour. A solution of 1-(isothiocyanatomethyl)-4-methoxybenzene (21.2 kg) in N,N-dimethylformamide (5 L) was added, and the reaction was stirred at 30-40° C. for 6-8 hours. After TLC showed that the reaction was completed, diisopropyl azodicarboxylate (12.9 kg) was added dropwise at 30-40° C. After completion of the dropwise addition, the reaction was stirred at 35-45° C. for 2 hours. After TLC showed that the reaction was completed, the reaction to solution was added with purified water (180 L) and stirred for 2-3 hours, and a large amount of light yellow solids were precipitated. The reaction mixture was filtrated by centrifugation, and spin-dried. The filter cake was washed with water and petroleum ether successively, filtrated and dried to obtain the title product (278.7 g, yield 110%).

(3) Preparation of 3-methoxy-1,2,4-thiadiazol-5-amine

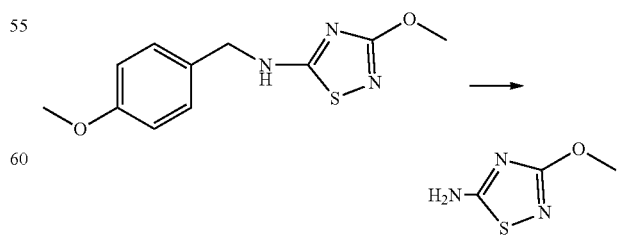

3-Methoxy-N-(4-methoxybenzyl)-1,2,4-thiadiazol-5-amine (12.4 kg) and trifluoroacetic acid (25 L) were added to a reaction flask under an argon atmosphere, and the reaction was stirred at 73-75° C. for 7-9 hours. After TLC showed that the reaction was completed, the reaction solution was concentrated under reduced pressure to obtain a brown liquid. The liquid was cooled to room temperature, and added with hydrochloric acid (1N, 5 L) and petroleum ether:ethyl acetate (5 L, V/V=1:1) under stirring. After stirring to dissolve, the reaction solution was filtrated, and the filter cake was washed with 1N hydrochloric acid (3 L×3). Two phases of the filtrate were separated, and the organic phase was back-extracted with 1N hydrochloric acid (25 L×3). The water phases were combined, filtrated by filter cloth and filter paper to remove insoluble solids. The filtrate was extracted with petroleum ether (25 L) again. The water phase was added with ethyl acetate (50 L), and the pH of the water phase was adjusted to 8-9 with solid potassium carbonate under stirring. Two phases were separated, and the water phase was extracted with ethyl acetate three times (30 L×3). The organic phases were combined and concentrated under reduced pressure to precipitate a large amount of white solids. The reaction mixture was cooled slightly, filtrated and dried to obtain the title product (45.8 g, yield 50%).

$^1$H-NMR (400 MHz, DMSO-$d_6$) δ 7.92 (s, 2H), 3.80 (s, 3H).

(4) Preparation of phenyl (3-methoxy-1,2,4-thiadiazol-5-yl)carbamate

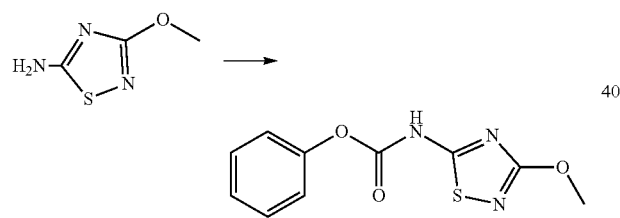

3-Methoxy-1,2,4-thiadiazol-5-amine (500 mg, 3.82 mmol) and phenyl chloroformate (600 mg, 3.82 mmol) were dissolved in dichloromethane (20 mL), then triethylamine (0.8 mL, 5.73 mmol) was added dropwise. After completion of the dropwise addition, the reaction solution was stirred for 16 hours, added with water (30 mL) to dilute, and two phases were separated. The water phase was extracted with dichloromethane (20 mL×2). The organic phases were combined, dried over anhydrous sodium sulfate, filtrated and concentrated under reduced pressure. The resulting residue was purified by silica gel column chromatography with eluent (dichloromethane and methanol) to obtain the title product phenyl (3-methoxy-1,2,4-thiadiazol-5-yl)carbamate (200 mg, yield 20.8%).

MS m/z (ESI): 252.2 [M+1]

$^1$H-NMR (400 MHz, CDCl$_3$) δ 12.33 (s, 1H), 7.46-7.42 (m, 2H), 7.33-7.26 (m, 3H), 4.01 (s, 3H).

Example 1. Preparation of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide (Compound IV)

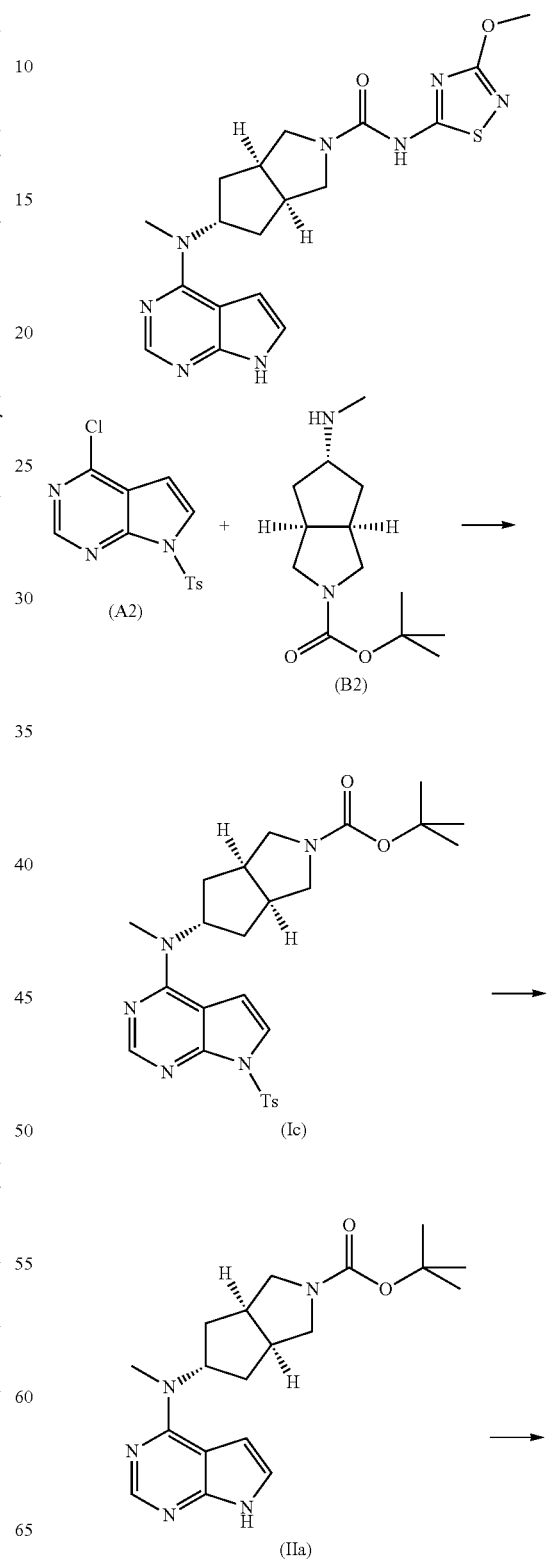

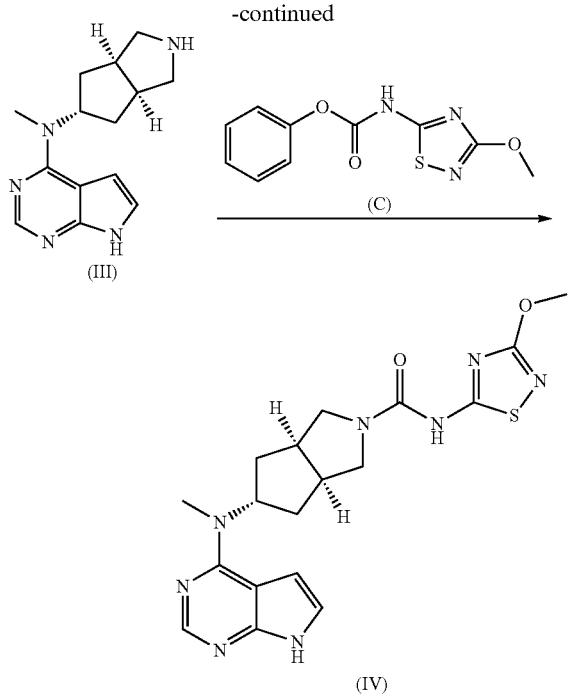

Step 1

Preparation of Tert-Butyl (3aR,5s,6aS)-5-(methyl(7-tosyl-7H-pyrrolo[2,3-d]pyrimidin-4-yl)amino)hexahydrocyclopenta[c]pyrrole-2(1H)-carboxylate (Ic)

4-Chloro-7-tosyl-7H-pyrrolo[2,3-d]pyrimidine (300 g, 0.98 mol), N—BOC-bicyclooctanone (234 g, 0.98 mol) and N,N-dimethylformamide (2.3 kg) were added to a reaction flask under a nitrogen atmosphere, and stirred to dissolve. The reaction solution was added with potassium carbonate (336 g, 2.44 mol), and warmed up to 100° C. under stirring for 2 hours. After TLC showed that the reaction was completed, the reaction solution was cooled to room temperature. The reaction solution was added with ice water (15 kg), and a large amount of khaki solids were precipitated. The reaction mixture was stirred at room temperature for 1 hour and filtrated, and the filter cake was dissolved in dichloromethane (6 kg) and extracted. The organic phase was dried over anhydrous sodium sulfate, filtrated and concentrated under reduced pressure to obtain a crude product. The crude product was dissolved in ethyl acetate (1.2 kg) under heating, and slowly added with petroleum ether (3.6 kg) at room temperature to precipitate a solid gradually. The reaction mixture was stirred for 1 hour and filtrated, and the filter cake was dried under reduced pressure to obtain the title product (349 g, yield 70.0%).

Step 2

Preparation of Tert-Butyl (3aR,5s,6aS)-5-(methyl (7H-pyrrolo[2,3-d]pyrimidin-4-yl)amino)hexahydrocyclopenta[c]pyrrole-2(1H)-carboxylate (IIa)

Tert-butyl (3aR,5s,6aS)-5-(methyl(7-tosyl-7H-pyrrolo[2,3-d]pyrimidin-4-yl)amino)hexahydrocyclopenta[c]pyrrole-2(1H)-carboxylate (315 g, 0.62 mol) and N,N-dimethylacetamide (1.5 kg) were added to a reaction flask and stirred to dissolve. The reaction solution was added with potassium hydroxide (176 g, 3.15 mol), then added with water (300 g) under stirring to precipitate a solid. The reaction mixture was warmed up to 70° C. and stirred to react for 1 hour. After TLC showed that the reaction was completed, the reaction solution was cooled to room temperature. The reaction solution was added with dichloromethane (3.9 kg) and water (3.0 kg), and extracted. Two phases were separated, and the organic phase was dried over anhydrous sodium sulfate and filtrated. The filtrate was concentrated under reduced pressure to obtain a light yellow solid, which was then added with a mixed solvent of ethyl acetate/petroleum ether (1.0 kg, v/v=1/4) and pulped under heating at 50° C. for 0.5 hour. The reaction mixture was filtrated and dried under reduced pressure to obtain the title product (192 g, yield 87.2%).

Step 3

Preparation of N-methyl-N-((3aR,5s,6aS)-octahydrocyclopenta[c]pyrrol-5-yl)-7H-pyrrolo[2,3-d]pyrimidin-4-amine (111)

Tert-butyl (3aR,5s,6aS)-5-(methyl(7H-pyrrolo[2,3-d]pyrimidin-4-yl)amino)hexahydrocyclopenta[c]pyrrole-2(1H)-carboxylate (187 g, 0.52 mol), anhydrous methanol and dichloromethane (0.8 kg, w/w=1.6) were added to a reaction flask and stirred to dissolve. Hydrochloric acid (0.55 kg, 15 mol) was added dropwise in an ice water bath. After completion of the addition, the reaction was stirred at room temperature for 10 hours. After TLC showed that the reaction was completed, the reaction solution was concentrated under reduced pressure to remove most of the organic solvent. The reaction solution was added with water (0.3 L) and extracted with dichloromethane (0.6 kg×3), and the organic phase was removed. The water phase was adjusted to the pH 9-10 by 30% sodium hydroxide solution, a large amount of solid was precipitated and filtrated. The solid was well pulped with purified water (0.25 kg×2), filtrated and dried under reduced pressure to obtain the title product (131 g, yield 97.3%).

Step 4

Preparation of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2 (1H)-carboxamide (compound IV)

N-methyl-N-((3aR,5s,6aS)-octahydrocyclopenta[c]pyrrol-5-yl)-7H-pyrrolo[2,3-d]pyrimidin-4-amine (101 g, 0.39 mol), phenyl (3-methoxy-1,2,4-thiadiazole-5-yl)carbamate (106 g, 0.42 mol) and tetrahydrofuran (1.8 kg) were added to a reaction flask under a nitrogen atmosphere, and stirred well. Triethylamine (170 g, 1.68 mol) was added. After completion of the addition, the reaction solution was heated to reflux and stirred for 5 hours. After TLC showed that the reaction was completed, the reaction solution was cooled to room temperature and filtrated. The filter cake was washed with tetrahydrofuran (400 g) and anhydrous ethanol (200 g), and dried under reduced pressure to obtain the title product (157 g, yield 96.5%).

Purity determined by HPLC: 99%
MS m/z (ESI): 415.2 [M+1]
$^1$H-NMR (400 MHz, DMSO-$d_6$) δ11.63 (s, 1H), 11.59 (s, 1H), 8.10 (s, 1H), 7.07 (m, 1H), 6.54-6.53 (m, 1H), 5.50-

5.46 (m, 1H), 3.91-3.87 (s, 3H), 3.73-3.60 (m, 2H), 3.37-3.33 (m, 2H), 3.19-3.16 (s, 3H), 2.89 (m, 2H), 2.05-1.97 (m, 2H), 1.81-1.76 (m, 2H).

Example 2. Preparation of (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide Disulfate

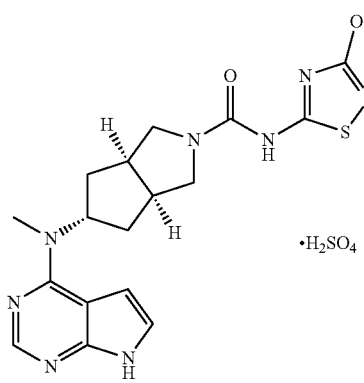

(1) Preparation of the Crude Product (3aR,5s,6aS)-N-(3-Methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide (140 g, 0.34 mol), anhydrous methanol (350 g) and dichloromethane (2.0 kg) were added to a reaction flask and stirred. Sulfuric acid (34.8 g, 0.36 mol) was slowly added dropwise at room temperature. The reaction solution was clear and stirred for 30 minutes, and filtrated to remove insoluble matters. The filtrate was concentrated under reduced pressure to obtain a solid, which was then added with anhydrous ethanol (700 mL) and stirred at room temperature for 4 hours. The reaction solution was filtrated and dried under reduced pressure to obtain crude (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide disulfate (160 g, yield 92.4%).

Purity determined by HPLC: 99%

(2) Purification of the Product

The crude (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide disulfate (145 g, 0.28 mol) and anhydrous methanol (11 kg) were added to a reaction flask. The reaction solution was heated to reflux until it was clear, then filtrated while it was still hot, and concentrated under reduced pressure. The concentrated solution was cooled to room temperature, stirred to precipitate a crystal and filtrated. The filter cake was washed with anhydrous ethanol (200 g), and dried under reduced pressure to obtain purified (3aR,5s,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide disulfate (138 g, yield 95.2%).

Purity determined by HPLC: 99.4%

MS m-z (ESI): 415.2 [M+1]

$^1$H-NMR (400 MHz, DMSO-$d_6$) δ 12.75 (s, 1H), 11.04 (s, 1H), 8.37 (s, 1H), 7.42-7.41 (t, 1H), 6.89 (s, 1H), 5.19-5.15 (m, 1H), 3.89 (s, 3H), 3.70-3.68 (m, 2H), 3.40-3.38 (m, 2H), 3.29 (s, 3H), 2.95 (s, 2H), 2.16-2.09 (m, 2H), 1.97-1.92 (m, 2H).

What is claimed is:

1. A compound of formula (I) or a stereoisomer thereof:

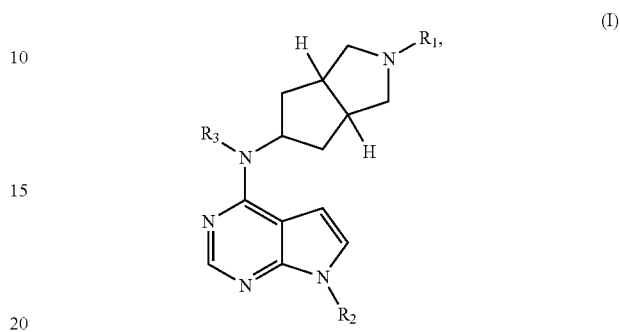

wherein, $R_1$ is hydrogen or an amino protecting group;

$R_2$ is an amino protecting group;

$R_3$ is selected from the group consisting of hydrogen, $C_{1-6}$ alkyl and an amino protecting group;

the amino protecting group is selected from the group consisting of alkoxycarbonyl amino protecting group, acyl amino protecting group, sulfonyl amino protecting group, and alkyl amino protecting group;

the alkoxycarbonyl amino protecting group is selected from the group consisting of benzyloxycarbonyl, tert-butoxycarbonyl, fluorenylmethoxycarbonyl, allyloxycarbonyl, trimethylsilylethoxycarbonyl, methoxycarbonyl, and ethoxycarbonyl;

the acyl amino protecting group is selected from the group consisting of phthalyl, trifluoroacetyl, pivaloyl, benzoyl, formyl, and acetyl;

the sulfonyl amino protecting group is selected from the group consisting of p-toluenesulfonyl, o-nitrobenzenesulfonyl, and p-nitrobenzenesulfonyl; and the alkyl amino protecting group is selected from the group consisting of trityl, 2,4-dimethoxybenzyl, p-methoxybenzyl, and benzyl.

2. The compound of formula (I) or a stereoisomer thereof according to claim 1, wherein, $R_1$ is an alkoxycarbonyl amino protecting group, and the alkoxycarbonyl amino protecting group is selected from the group consisting of benzyloxycarbonyl, tert-butoxycarbonyl, fluorenylmethoxycarbonyl, and allyloxycarbonyl;

$R_2$ is a sulfonyl amino protecting group, and the sulfonyl amino protecting group is selected from the group consisting of p-toluenesulfonyl, o-nitrobenzenesulfonyl, and p-nitrobenzenesulfonyl; and $R_3$ is selected from the group consisting of hydrogen and methyl.

3. The compound of formula (I) or a stereoisomer thereof according to claim 1, wherein the compound has a structure of formula (Ia) below,

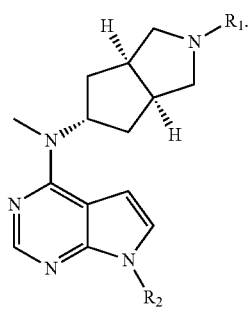
(Ia)

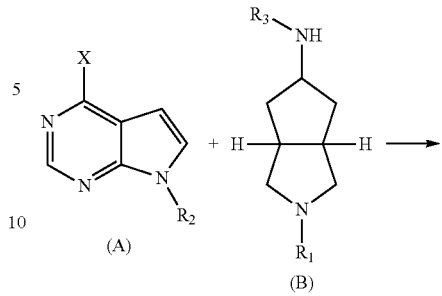
(A)  (B)

4. The compound of formula (I) or a stereoisomer thereof according to claim 1, wherein the compound has a structure of formula (Ib) below,

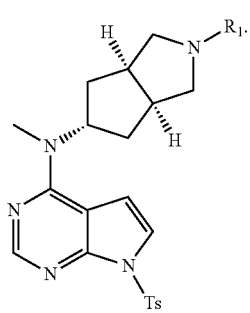
(Ib)

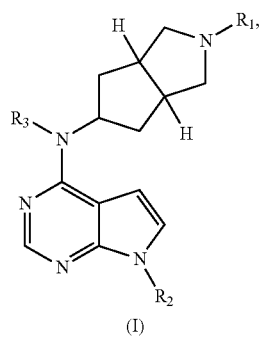
(I)

wherein, X is halogen.

7. The method according to claim 6, characterized in that the method is a reaction of a compound of formula (A) with a compound of formula (B1) to obtain a compound of formula (Ia),

5. The compound of formula (I) or a stereoisomer thereof according to claim 1, wherein the compound has a structure of formula (Ic) below,

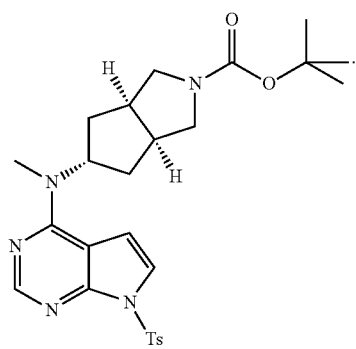
(Ic)

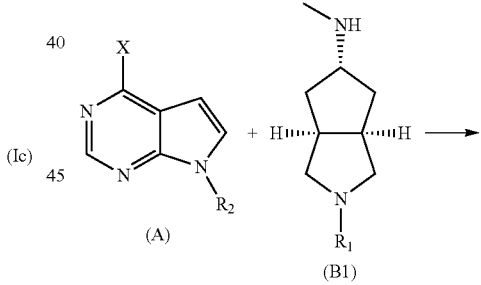
(A)  (B1)

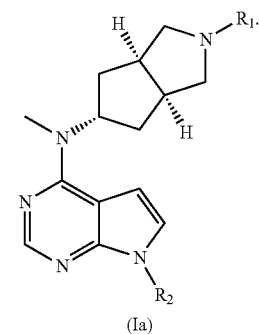
(Ia)

6. A method for preparing the compound of formula (I) according to claim 1, characterized in that the method comprises a step of reacting a compound of formula (A) with a compound of formula (B),

8. The method according to claim 7, characterized in that the method is a reaction of a compound of formula (A1) with a compound of formula (B1) to obtain a compound of formula (Ib),

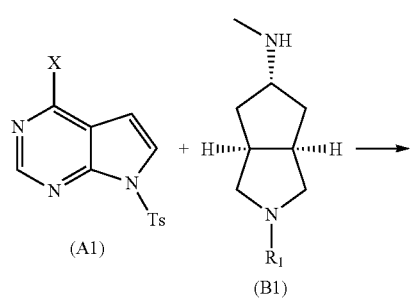

(A1) + (B1) →

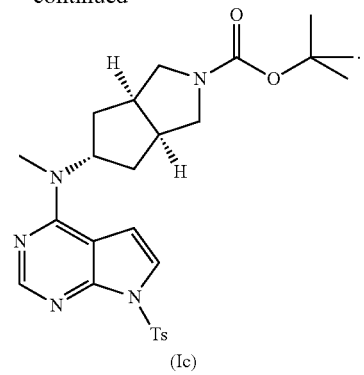

(Ic)

10. A compound of formula (I') or a stereoisomer thereof:

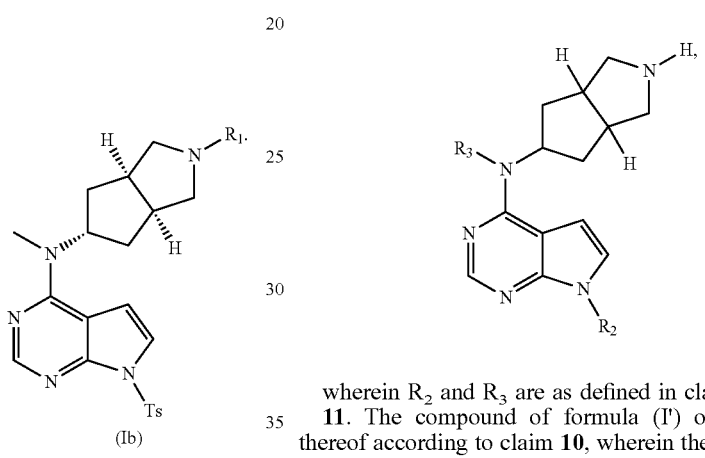

(I')

wherein $R_2$ and $R_3$ are as defined in claim 1.

11. The compound of formula (I') or a stereoisomer thereof according to claim 10, wherein the compound has a structure of formula (I'-1) below,

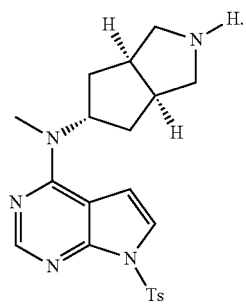

(I'-1)

9. The method according to claim 8, characterized in that the method is a reaction of a compound of formula (A2) with a compound of formula (B2) to obtain a compound of formula (Ic),

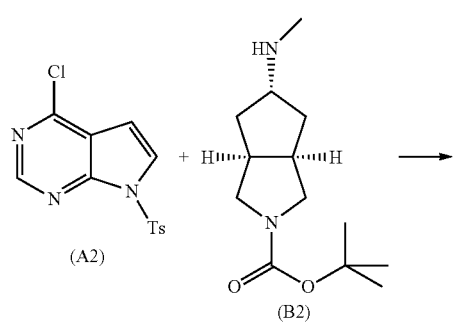

12. The compound of formula (I) or a stereoisomer thereof according to claim 2, wherein, $R_2$ is p-toluenesulfonyl.

* * * * *